(12) United States Patent
Beery et al.

(10) Patent No.: US 12,390,206 B2
(45) Date of Patent: Aug. 19, 2025

(54) COMPRESSOR/DISTRACTOR WITH TOWER TRAVERSAL

(71) Applicant: Thompson Surgical Instruments, Inc., Traverse City, MI (US)

(72) Inventors: Zach Beery, Traverse City, MI (US); William White, Traverse City, MI (US)

(73) Assignee: THOMPSON SURGICAL INSTRUMENTS, INC., Traverse City, MI (US)

( * ) Notice: Subject to any disclaimer, the term of this patent is extended or adjusted under 35 U.S.C. 154(b) by 0 days.

(21) Appl. No.: 18/072,236

(22) Filed: Nov. 30, 2022

(65) Prior Publication Data
US 2024/0173022 A1 May 30, 2024

(51) Int. Cl.
*A61B 17/02* (2006.01)
*A61B 17/00* (2006.01)

(52) U.S. Cl.
CPC .............. *A61B 17/0206* (2013.01); *A61B 2017/00407* (2013.01)

(58) Field of Classification Search
CPC . A61B 17/68; A61B 2017/681; A61B 17/025; A61B 17/66; A61B 17/861
See application file for complete search history.

(56) References Cited

U.S. PATENT DOCUMENTS

| | | | |
|---|---|---|---|
| 6,033,363 A | 3/2000 | Farley et al. | |
| 6,511,423 B2 | 1/2003 | Farley | |
| 6,746,467 B1 | 6/2004 | Taylor | |
| 7,582,058 B1 | 9/2009 | Miles | |
| 7,931,591 B2 | 4/2011 | McCarthy et al. | |
| 8,062,218 B2 | 11/2011 | Sebastian et al. | |
| 8,636,655 B1 | 1/2014 | Childs | |
| 9,066,701 B1 | 6/2015 | Finley et al. | |
| 9,095,301 B2 | 8/2015 | Hamada | |
| 9,314,152 B2 | 4/2016 | Pimenta et al. | |
| 9,351,718 B1 | 5/2016 | Arambula et al. | |
| 9,380,932 B1 | 7/2016 | Lynn et al. | |
| 9,622,732 B2 | 4/2017 | Martinelli et al. | |
| 9,730,683 B2 | 8/2017 | Reimels | |
| 9,826,966 B2 | 11/2017 | Mast et al. | |
| 10,039,539 B2 | 8/2018 | Friedrich et al. | |
| 10,278,786 B2 * | 5/2019 | Friedrich | ........... A61B 17/0206 |
| 10,285,680 B2 * | 5/2019 | Friedrich | ................. A61B 1/32 |
| 10,357,238 B2 | 7/2019 | Miles et al. | |

(Continued)

FOREIGN PATENT DOCUMENTS

KR 20120075711 7/2012

*Primary Examiner* — Eduardo C Robert
*Assistant Examiner* — Holly Joanna Lane
(74) *Attorney, Agent, or Firm* — McAndrews, Held & Malloy, Ltd.

(57) ABSTRACT

A surgical instrument includes a rack, a first arm coupled to the rack, a second arm coupled to the rack, a first tower coupled to the first arm, and a second tower coupled to the second arm. The first tower comprises an upper end, a lower end, and a track between the upper end and the lower end. A channel of the first arm is configured to receive the track of the first tower and selectively position the first arm along the track of the first tower. The lower end of the first tower is configured to snap onto a pedicle screw and to disengage from the pedicle screw in response to a removal tool being inserted into the first tower.

30 Claims, 14 Drawing Sheets

(56) References Cited

U.S. PATENT DOCUMENTS

| | | |
|---|---|---|
| 10,499,896 B2 * | 12/2019 | Abidin ............... A61B 17/8891 |
| 10,603,026 B2 | 3/2020 | Cryder et al. |
| 10,695,044 B2 | 6/2020 | Miles et al. |
| 10,869,657 B2 * | 12/2020 | Raymond ............... A61B 17/02 |
| 10,980,576 B2 * | 4/2021 | Woolley ............. A61B 17/7076 |
| 11,103,227 B2 | 8/2021 | Baudouin et al. |
| 11,116,489 B2 | 9/2021 | Kim |
| 11,154,288 B1 | 10/2021 | Lovell et al. |
| 11,219,437 B2 | 1/2022 | Miles et al. |
| 11,224,415 B1 | 1/2022 | Josse |
| 11,272,912 B2 * | 3/2022 | Heiges ............... A61B 17/0218 |
| 11,399,816 B2 * | 8/2022 | O'Connell ......... A61B 17/0218 |
| 11,432,810 B2 | 9/2022 | Gregersen et al. |
| 11,457,907 B2 | 10/2022 | Lee et al. |
| 11,457,910 B1 | 10/2022 | Lynch et al. |
| 11,478,237 B2 * | 10/2022 | Spann ............... A61B 17/0206 |
| 11,504,107 B2 | 11/2022 | Cianfrani et al. |
| 11,564,674 B2 | 1/2023 | Hill et al. |
| 11,607,209 B2 | 3/2023 | O'Connell et al. |
| 11,627,952 B2 * | 4/2023 | Eckhof .................. A61B 17/86 |
| | | 600/213 |
| 2002/0077531 A1 | 6/2002 | Puchovsky |
| 2004/0176665 A1 | 9/2004 | Branch |
| 2005/0070765 A1 | 3/2005 | Abdelgany |
| 2007/0021656 A1 | 1/2007 | Martin |
| 2008/0058606 A1 | 3/2008 | Miles |
| 2009/0259107 A1 | 10/2009 | Crenshaw |
| 2009/0275804 A1 | 11/2009 | Bertagnoli |
| 2010/0217089 A1 | 8/2010 | Farley |
| 2010/0222644 A1 | 9/2010 | Sebastian et al. |
| 2012/0136215 A1 | 5/2012 | Farley |
| 2016/0287236 A1 | 10/2016 | Garcia-Bengochea et al. |
| 2018/0206834 A1 | 7/2018 | Villamil et al. |
| 2018/0249992 A1 * | 9/2018 | Truckey ............... A61B 17/025 |
| 2019/0216450 A1 | 7/2019 | Bjork et al. |
| 2021/0220009 A1 | 7/2021 | Heiges et al. |
| 2022/0079573 A1 | 3/2022 | Ortiz et al. |
| 2022/0202404 A1 | 6/2022 | Rajek |
| 2022/0265256 A1 * | 8/2022 | Villamil ............... A61F 2/4601 |
| 2022/0401092 A1 | 12/2022 | Stiefferman et al. |

* cited by examiner

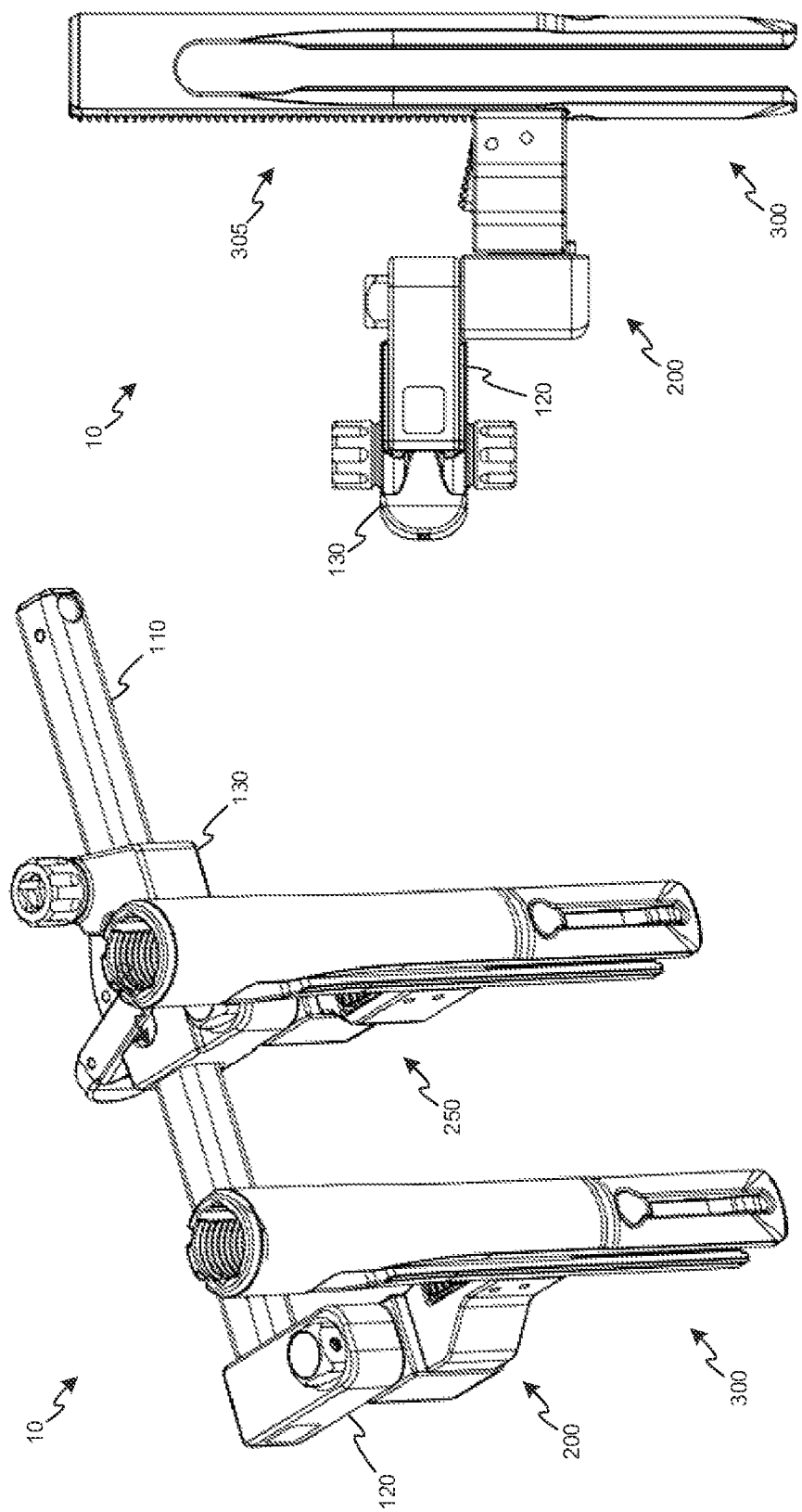

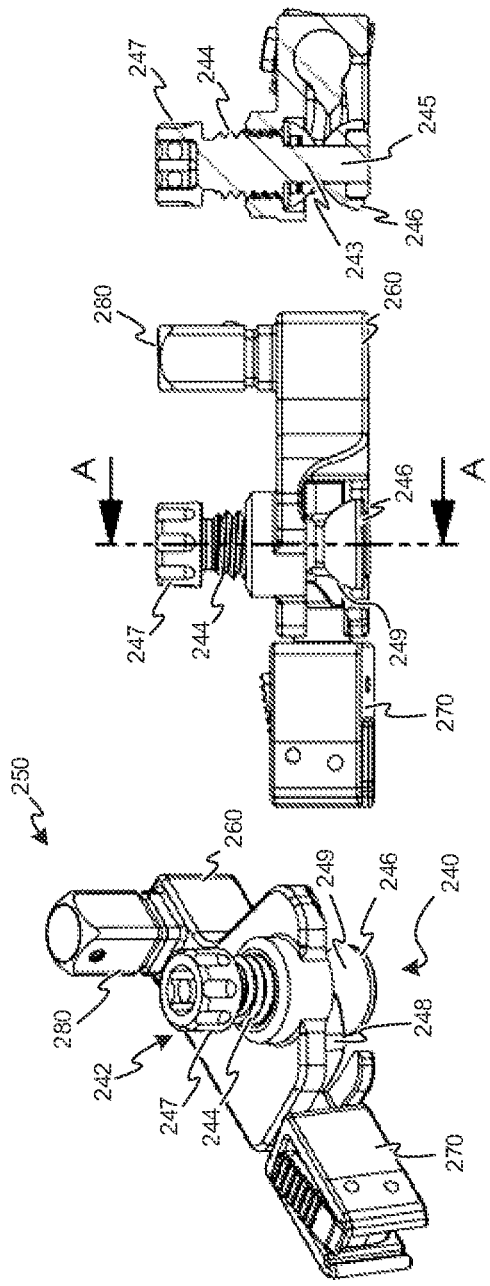
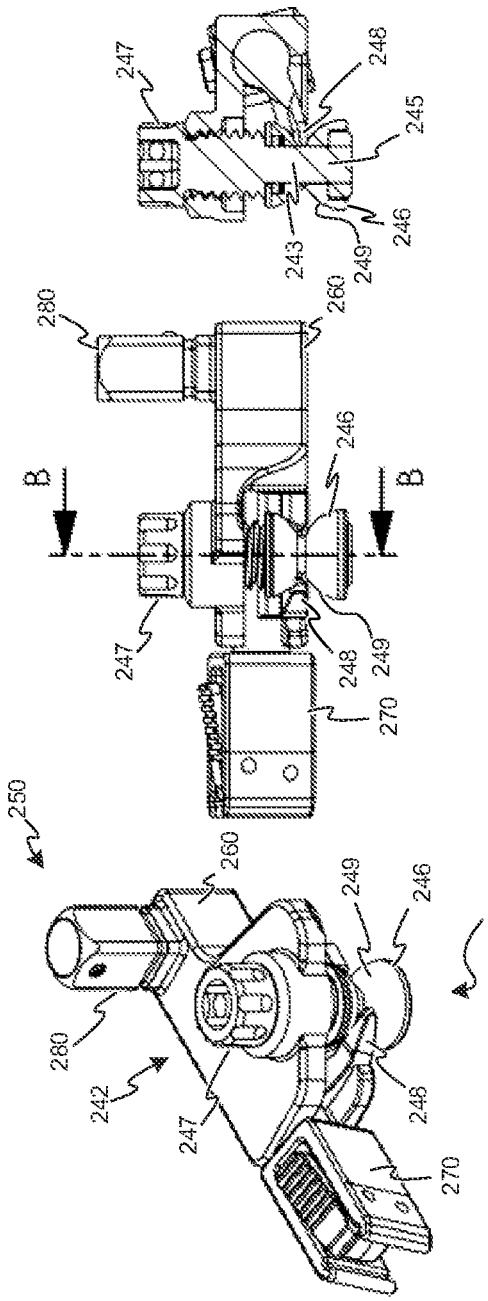

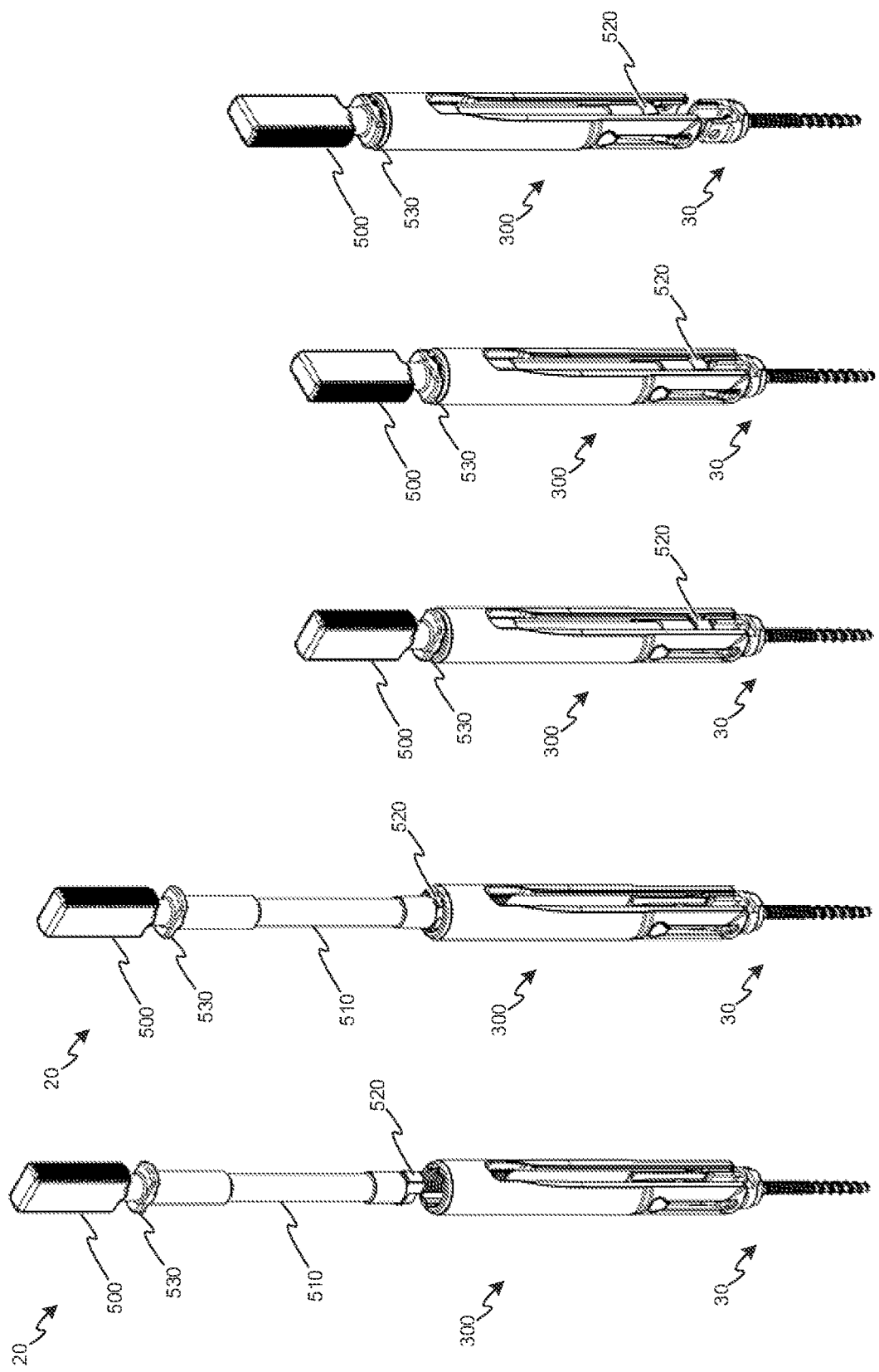

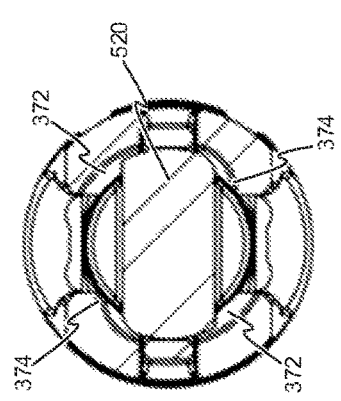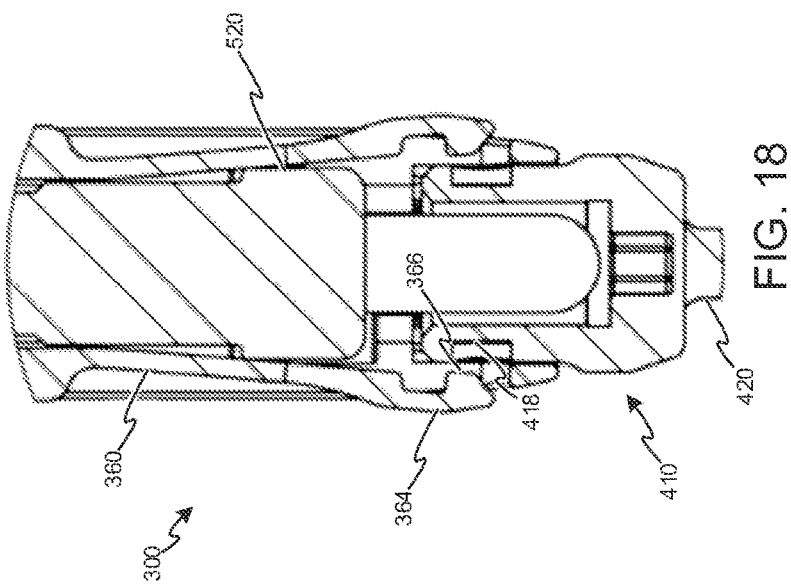
FIG. 18
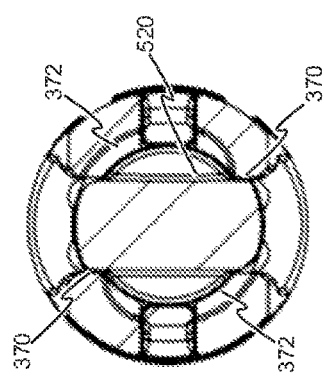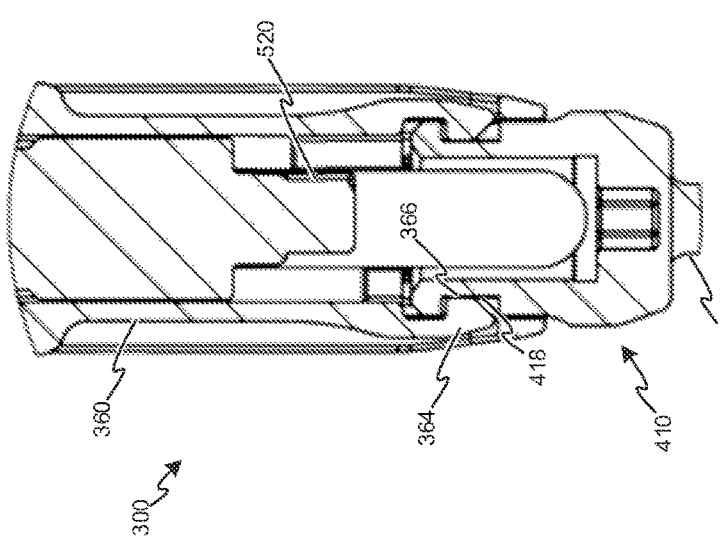
FIG. 17

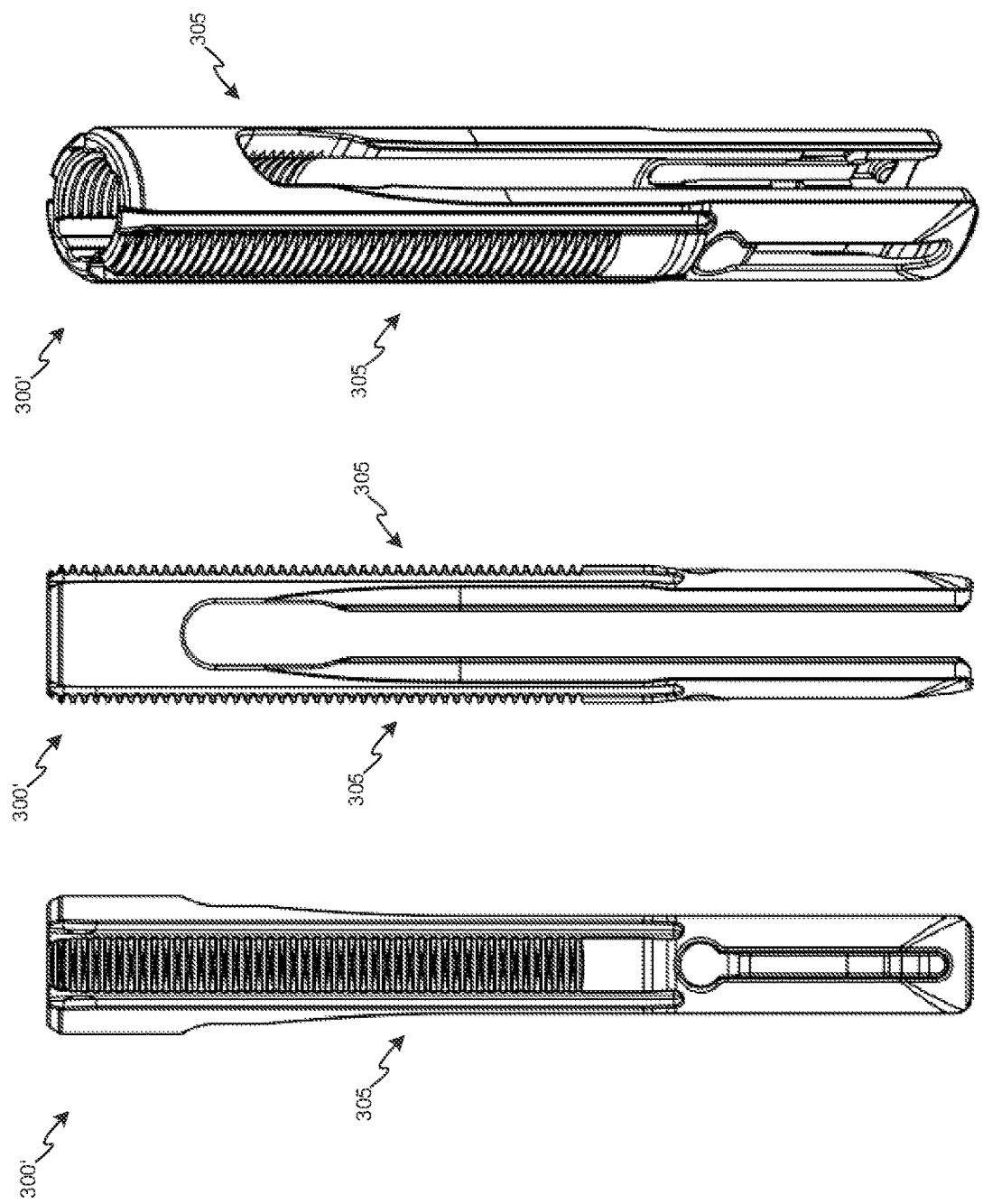

COMPRESSOR/DISTRACTOR WITH TOWER TRAVERSAL

BACKGROUND

The present disclosure relates to a surgical apparatus and in particular to a compressor/distractor instrument that applies compression forces and/or distraction forces on anatomical structures.

For example, pedicle screws may be inserted into vertebrae of a defective region. Spinal fixation rods may rigidly fix the vertebrae relative to one another between the pedicle screws. A compressor/distractor instrument may be coupled to the pedicle screws and may apply compression forces and/or distraction forces to the vertebrae via the pedicle screws. Via such compression forces and/or distraction forces the attached vertebrae may be appropriately positioned.

Further limitations and disadvantages of conventional and traditional approaches will become apparent to one of skill in the art, through comparison of such approaches with the present disclosure as set forth in the remainder of the present application with reference to the drawings.

SUMMARY

Various aspects of this disclosure provide a surgical instrument, such as a compressor/distractor instrument, that may apply compression forces and/or distraction forces to anatomical structures. For example and without limitation, various aspects of the disclosure are directed to a surgical instrument comprising a rack, arms coupled to the rack, and towers coupled to the arms. Each tower may comprise a longitudinal track that extends between an upper end of the tower and a lower end of the tower. An arm may be coupled to a tower via its respective longitudinal track. The longitudinal track may permit the arm to traverse or translate longitudinally along the tower. In various embodiments, the longitudinal track permits the arm to be selectively positioned along the tower and locked into such selected position.

Furthermore, a lower end of each tower may snap onto a head of a pedicle screw that has been affixed to an anatomical structure. Thus, the tower may permit a simple manner for attaching the surgical instrument to the anatomical structure via affixed pedicle screws. Moreover, while the tower may simply snap onto a pedicle screw without the aid of a tool, the tower may require the use of a tool to detach the tower from the pedicle screw. Such configuration reduces the likelihood of the tower being accidentally detached from the pedicle screw.

Further aspects will become apparent to one of skill in the art through review of the present disclosure and referenced drawings.

BRIEF DESCRIPTION OF THE DRAWINGS

FIG. 7 provides a perspective view of the surgical instrument depicted in FIG. 1 with its arms in a lowered position.

FIG. 8 provides a side view of the surgical instrument depicted in FIG. 1 with its arms in a lowered position.

FIGS. 12A-12F provide various views of another embodiment of a pivot joint that permits angling of such arm per FIGS. 9 and 10.

FIG. 15A-15E depict a removal tool and a process of using the removal tool to disengage a tower of the surgical instrument of FIG. 1 from a pedicle screw.

FIG. 17 provides a lateral cross-section and longitudinal cross-section depicting the removal tool seated in the tower of the surgical instrument of FIG. 1.

FIG. 18 provides a lateral cross-section and longitudinal cross-section depicting the removal tool disengaging the tower of the surgical instrument of FIG. 1 from a pedicle screw.

FIGS. 23A-23C provide various views depicting the multiple tracks of the towers shown in FIGS. 21 and 22.

DETAILED DESCRIPTION

Figure 2:
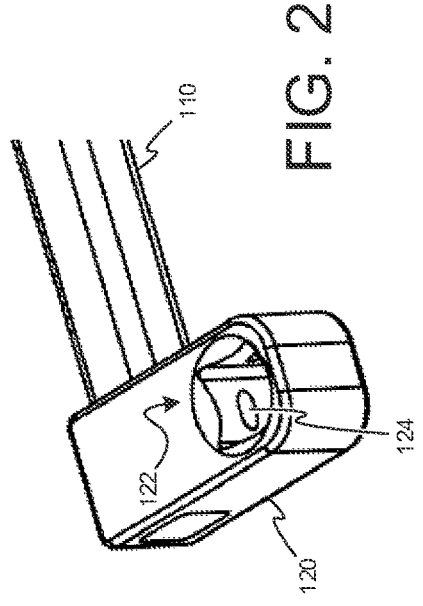
FIG. 2 depicts an arm connector of the surgical instrument depicted in FIG. 1.

The following discussion presents various aspects of the present disclosure by providing examples thereof. Such examples are non-limiting, and thus the scope of various aspects of the present disclosure should not necessarily be limited by any particular characteristics of the provided examples. In the following discussion, the phrases "for example," "e.g.," and "exemplary" are non-limiting and are generally synonymous with "by way of example and not limitation," "for example and not limitation," and the like.

As utilized herein, "and/or" means any one or more of the items in the list joined by "and/or". As an example, "x and/or y" means any element of the three-element set {(x), (y), (x, y)}. In other words, "x and/or y" means "one or both of x and y." As another example, "x, y, and/or z" means any element of the seven-element set {(x), (y), (z), (x, y), (x, z), (y, z), (x, y, z)}. In other words, "x, y and/or z" means "one or more of x, y, and z."

The terminology used herein is for the purpose of describing particular examples only and is not intended to be limiting of the disclosure. As used herein, the singular forms are intended to include the plural forms as well, unless the context clearly indicates otherwise. It will be further understood that the terms "comprises," "includes," "comprising," "including," "has," "have," "having," and the like when used in this specification, specify the presence of stated features, integers, steps, operations, elements, and/or components, but do not preclude the presence or addition of one or more other features, integers, steps, operations, elements, components, and/or groups thereof.

It will be understood that, although the terms first, second, etc. may be used herein to describe various elements, these elements should not be limited by these terms. These terms are only used to distinguish one element from another element. Thus, for example, a first element, a first component or a first section discussed below could be termed a second element, a second component or a second section without departing from the teachings of the present disclosure. Similarly, various spatial terms, such as "upper," "lower," "side," and the like, may be used in distinguishing one element from another element in a relative manner. It should be understood, however, that components may be oriented in different manners, for example a semiconductor device may be turned sideways so that its "top" surface is facing horizontally and its "side" surface is facing vertically, without departing from the teachings of the present disclosure.

In the drawings, various dimensions (e.g., layer thickness, width, etc.) may be exaggerated for illustrative clarity. Additionally, like reference numbers are utilized to refer to like elements through the discussions of various examples.

The discussion will now refer to various example illustrations provided to enhance the understanding of the various aspects of the present disclosure. It should be understood that the scope of this disclosure is not limited by the specific characteristics of the examples provided and discussed herein.

FIGS. 1-14 provide different views of a surgical instrument 10 and how the surgical instrument 10 may interact with pedicle screws 30 that may be affixed to anatomical structures. FIGS. 15-18 depict a removal tool 20 and how the removal tool 20 may interact with towers 300 of the surgical instrument 10 so as to detach or unlock the towers 300 from pedicle screws 30. In various embodiments, the surgical instrument 10 may be implemented as a compressor/distractor instrument, which may be attached to anatomical structures via pedicle screws 30 in order to selectively apply a compression force or a distraction force to such anatomical structures. However, aspects of the surgical instrument 10 may be embodied in a compressor instrument configured to provide a compression force but not a distraction force. Similarly, aspects of the surgical instrument 10 may be embodied in a distractor instrument configured to provide a distraction force but not a compression force.

Figure 1:
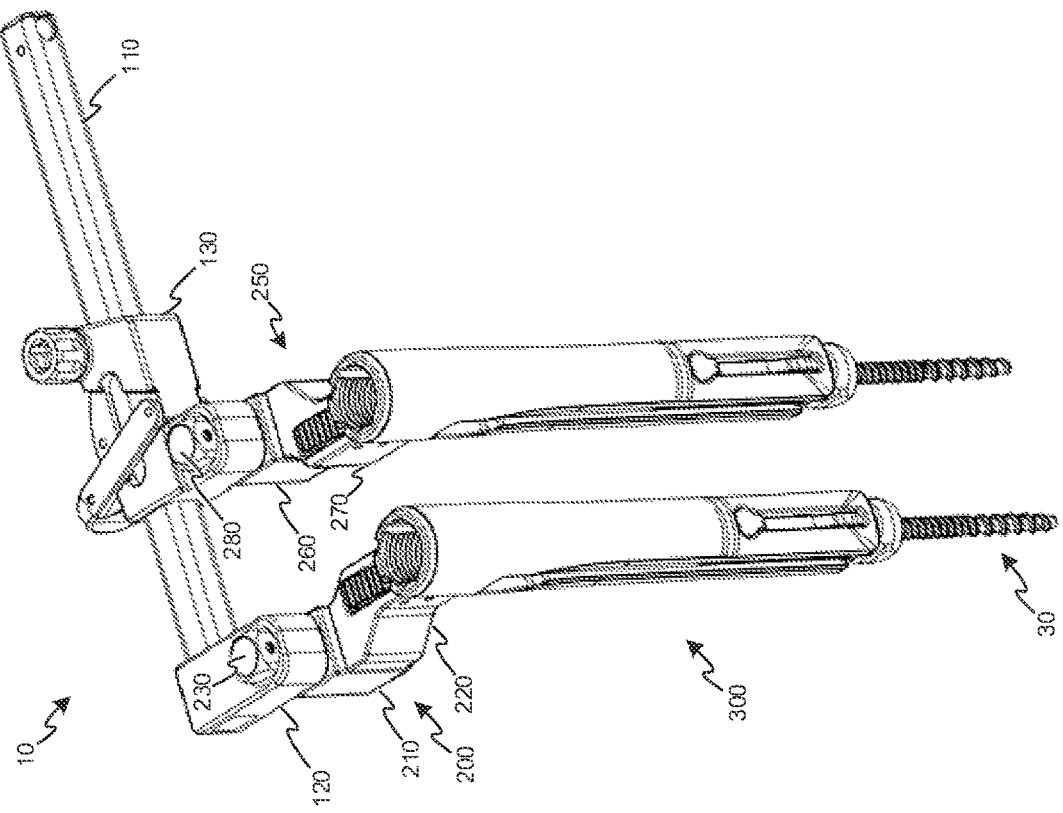
FIG. 1 provides a perspective view of a surgical instrument in accordance with various aspects of the present disclosure.

Referring now to FIG. 1, a perspective view of the surgical instrument 10 is provided. As shown, the surgical instrument 10 may include a rack 110, an arm connector 120, an arm carriage 130, a first arm 200, a second arm 250, and towers 300. A proximal portion 210 of the first arm 200 is coupled to the rack 110 via the arm connector 120. Further, a distal portion 220 of the first arm 200 is coupled to a first tower 300. Similarly, a proximal portion 260 of the second arm 250 is coupled to the rack 110 via the arm carriage 130. A distal portion 270 of the second arm 250 is coupled to a second tower 300. In various embodiments, the first tower 300 is identical to the second tower 300 and thus interchangeable during use. Moreover, one or more parts of the surgical instrument 10 may be formed from surgical stainless steel. Other embodiments may utilize various alternative materials to form all or part of surgical instrument 10.

As further shown in FIG. 1, lower ends of the towers 300 may engage pedicle screws 30 in order to impart compression forces and/or distraction forces to affixed anatomical structures. As explained in greater detail below, the towers 300 are effectively locked to the pedicle screws 30. In order to disengage the towers 300 from the pedicle screws 30, a person uses a separate removal tool 20 to release the towers 300 from their respective pedicle screws 30. By requiring a separate removal tool 20, the towers 300 may effectively prevent inadvertent disengagement from the pedicle screws 30 and corresponding anatomical structures during a surgical procedure.

Figure 4:
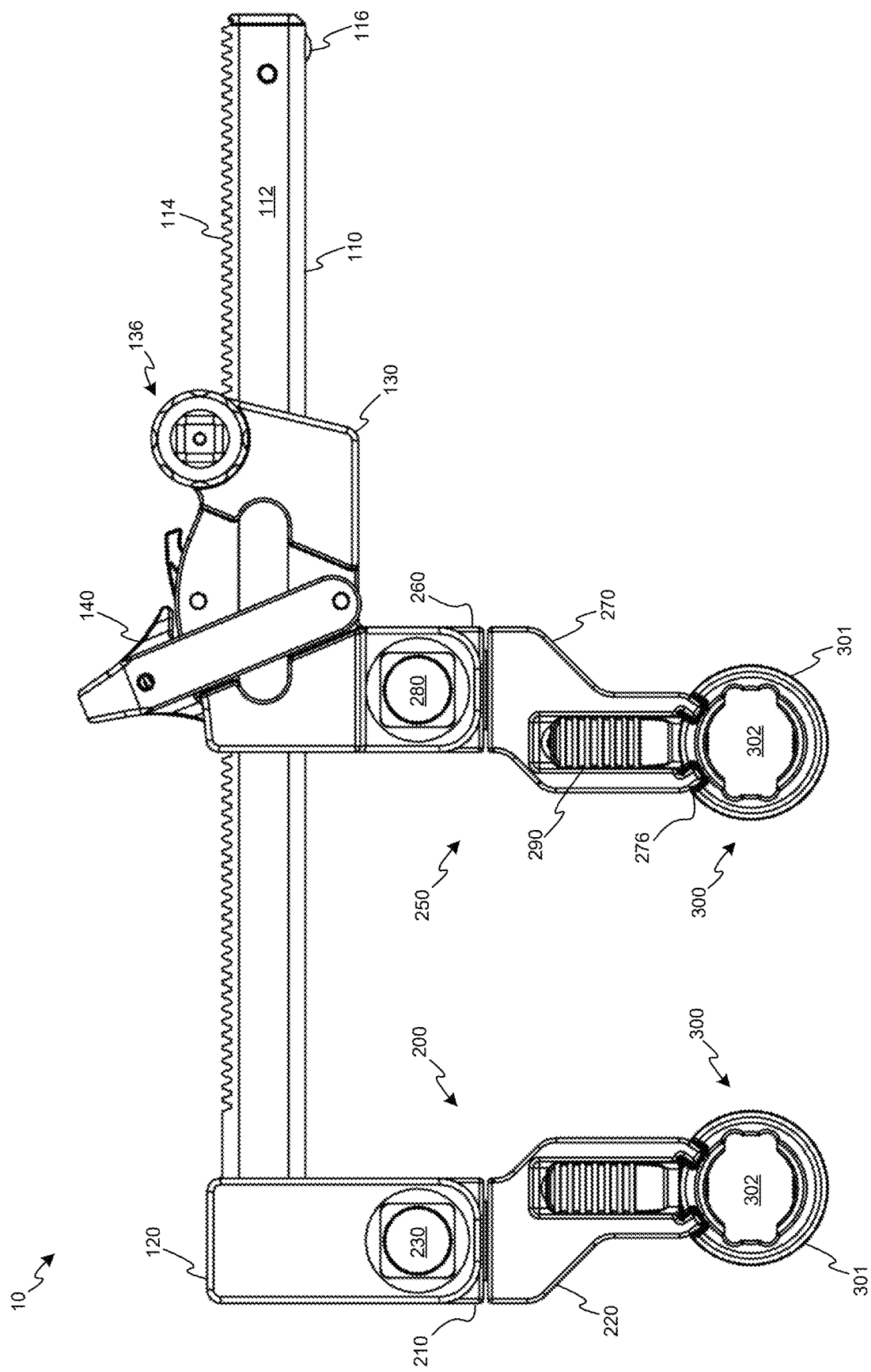
FIG. 4 provides a top view of the surgical instrument depicted in FIG. 1.

As shown in FIG. 4, the rack 110 may comprise a cylindrical rod or rail 112 having a rectangular cross section. Moreover, the rail 112 may include teeth 114 spanning a longitudinal rear surface of the rail 112 and a stop 116 toward a free end of the rail 112. In various embodiments, an internal spring (not shown) biases the stop 116 such that the stop 116 protrudes from a front surface of the rail 112. The protruding stop 116 may prevent the arm carriage 130 from falling off the free end of the rail 112. In particular, the internal spring may apply a biasing force to the stop 116 that is sufficient to prevent the arm carriage 130 from sliding past the stop 116 and off the free end of the rail 112 under its own weight. However, the biasing force provided by the spring may be overcome by a person imparting additional force to arm carriage 130 which causes retraction of the stop 116 into the rack 110, thus permitting the person to slide the arm carriage 130 past the stop 116 and off the free end of the rack 110.

Referring now to FIGS. 1 and 2, the arm connector 120 may be affixed to an end of the rack 110 in a stationary manner. However, in some embodiments, the arm connector 120 may be replaced with an arm carriage similar to the arm carriage 130 so as to permit translation of both the first arm 200 and the second arm 250 along the rack 110. As shown, the arm connector 120 may include a port 122. The port 122 may have a non-circular cross section that closely mates with a post 230 of the first arm 200. As shown, one or more walls of the port 122 may have a recess 124 configured to receive a detent of the post 230.

Figure 3:
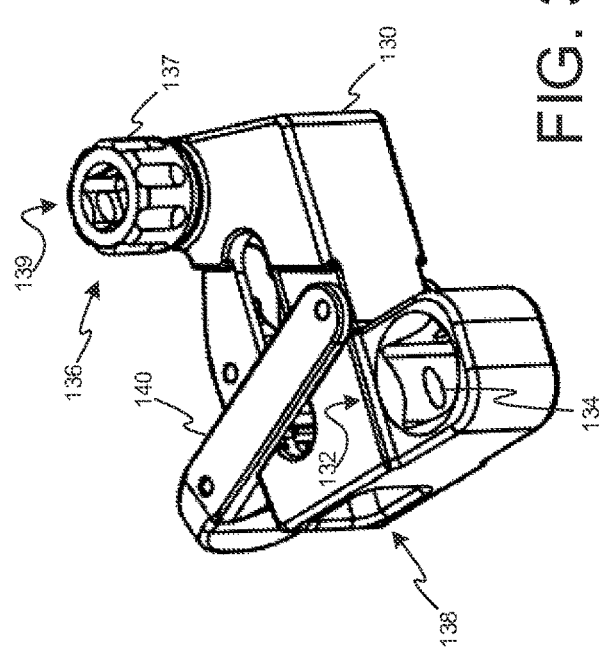
FIG. 3 depicts an arm carriage of the surgical instrument depicted in FIG. 1.

Similarly, as shown in FIG. 3, the arm carriage 130 may include a port 132. The port 132 may have a non-circular cross section that closely mates with a post 280 of the second arm 250. One or more walls of the port 132 may have a recess 134 configured to receive a detent of the post 280.

The arm carriage 130 may include a pinion 136. The pinion 136 may include a head 137 and teeth that engage the teeth 114 of the rack 110. The head 137 may include a socket 139 to receive a tool, which may rotate the pinion 136. Through rotation of the pinion 136 and its engagement with teeth 114, the pinion 136 may impart ratcheted-movement of the arm carriage 130 along the rack 110. In particular, rotation of the pinion 136 in a first direction may cause the arm carriage 130 to traverse along the rack 110 toward the stationary arm connector 120 and impart a compression force between the arms 200, 250 coupled to the arm connector 120 and the arm carriage 130. Conversely, rotation of the pinion 136 in a second direction opposite the first direction may cause the arm carriage 130 to traverse along the rack 110 away from the arm connector 120 and impart a distraction force between the arms 200, 250 coupled to the arm connector 120 and the arm carriage 130. To this end, the rack 110 may pass through a longitudinal aperture 138 of the arm carriage 130.

As shown, the arm carriage 130 may further include a lever 140 that may be selectively moved among a compression position, a distraction position, and a disengaged position. When placed in the compression position, the lever 140 positions a first pawl such that the first pawl is moved toward and engages teeth 114 of the rack 110 and positions the second pawl such that the second pawl is moved away from and disengages the teeth 114 of the rack 110. Conversely, when placed in the distraction position, the lever 140 positions the first pawl such that the first pawl is moved away from and disengages teeth 114 of the rack 110 and positions the second pawl such that the second pawl is moved toward and engages the teeth 114 of the rack 110. Further, when placed in the disengaged position, the lever 140 positions the first pawl such that the first pawl is moved away from and disengages teeth 114 of the rack 110 and positions the second pawl such that the second pawl is moved away from and disengages the teeth 114 of the rack 110. Due to such disengagement of the pawls, the arm carriage 130 in various embodiments may freely slide along the rack 110 when the lever 140 is in placed in the disengaged position.

In various embodiments, the first pawl and teeth 114 permit ratcheted movement in the compression direction when the first pawl is engaged with the teeth 114. Moreover, while engaged, the first pawl and teeth 114 may prevent movement in the opposite distraction direction. To this end, the teeth 114 of the rack 110 in various embodiments are uniformly-shaped and symmetrically-sloped, with leading and trailing edges having the same slope. However, the first pawl is not symmetrically sloped. Instead, the leading edge (i.e., edge toward the compression direction of ratcheted movement) is more moderately-sloped than the opposite trailing edge. As a result of the more moderately-sloped or less steeply-sloped leading edge, lateral movement of the arm carriage 130 with respect to the rack 110 in the compression direction imparts an upward force upon the first pawl that is sufficient to overcome the biasing force of an associated spring and permit the first pawl to travel over the teeth 114. Conversely, as a result of the more steeply-sloped trailing edge, lateral movement of the arm carriage 130 with respect to the rack 110 in the distraction direction fails to impart an upward force upon the first pawl that is sufficient to overcome the biasing force of the spring, thus preventing the first pawl from traveling over the teeth 114. In this manner, the arm carriage 130 may lock or retain its attached retractor arm 250 to a particular location along the rack 110, thereby maintaining a desired compression force between the arms 200, 250.

In various embodiments, the second pawl and teeth 114 may permit ratcheted movement in the distraction direction when engaged. Moreover, while engaged, the second pawl and teeth 114 may prevent movement in the opposite compression direction. To this end, the second pawl may be implemented in a similar manner as the first pawl. Namely, the leading edge (i.e., edge toward the distraction direction of ratcheted movement) is more moderately-sloped than the opposite trailing edge.

Figures 5, 6:
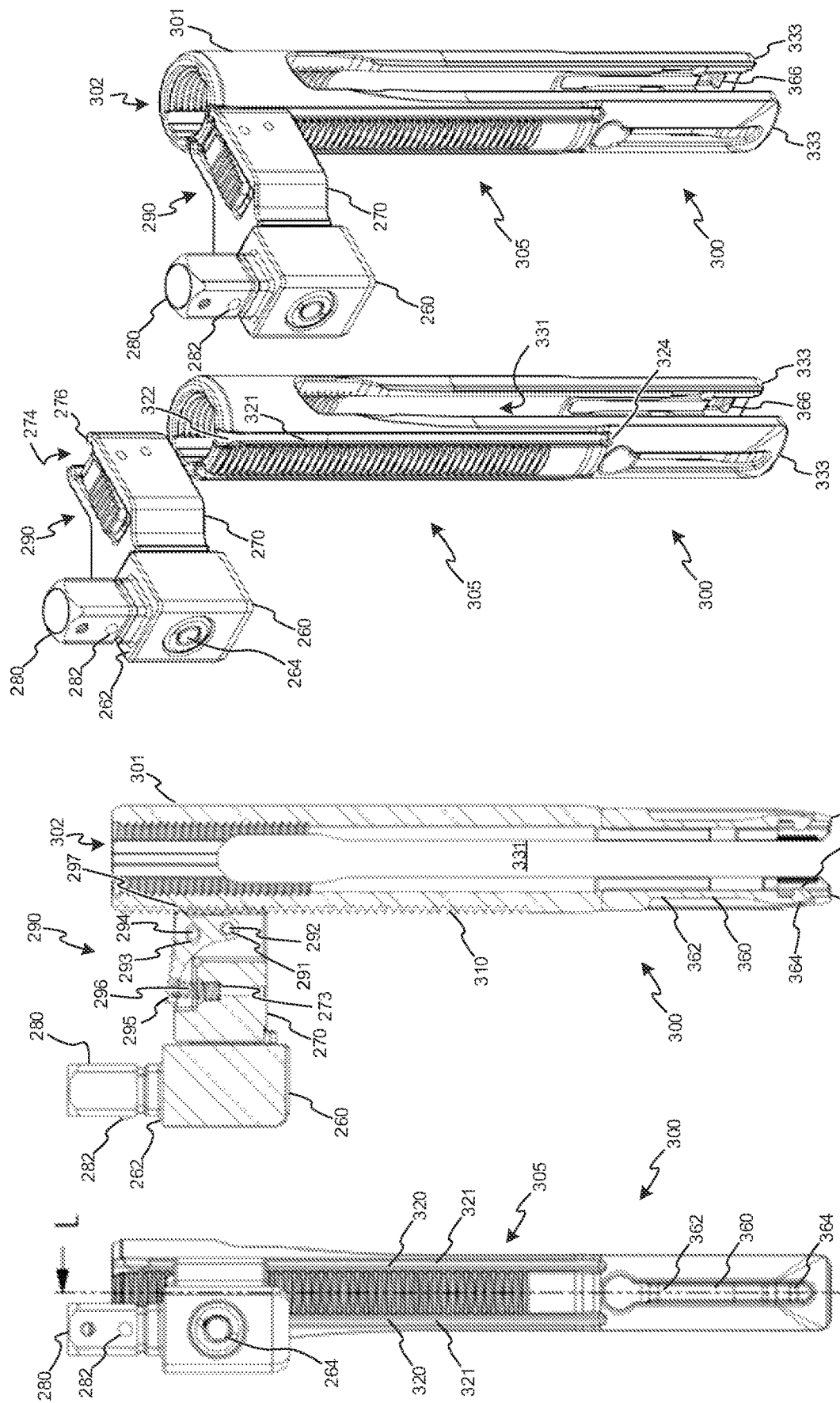
FIG. 5 provides a front view and correspond cross-section of an arm and tower of the surgical instrument depicted in FIG. 1.
FIG. 6 provides perspective views of an arm and tower of the surgical instrument depicted in FIG. 1.

Referring now to FIGS. 4-6, aspects of the arms 200, 250 will be described. In various embodiments, the only substantive difference between the first arm 200 and second arm 250 is the angle or offset of the distal portion 220, 270 of the respective arm 200, 250 with respect to its proximal portion 210, 260. Namely, the distal portion 220 of the first arm 200 is angled or offset from its proximal portion 210 toward the free end of the rack 110 whereas the distal portion 270 of the second arm 250 is angled or offset from its proximal portion 260 toward the opposite end of the rack 110. Thus, in various embodiments, the first arm 200 essentially mirrors the second arm 250. As such, the following discussion focuses mainly on the second arm 250 as depicted in FIGS. 5 and 6. However, the first arm 200 may be implemented in a similar manner.

As shown, the proximal portion 260 of the arm 250 may include a post 280 that protrudes above a top surface 262 of the proximal portion 260. The post 280 may have a non-circular cross section that closely mates with a port 122 of the arm connector 120 or the port 132 of the arm carriage 130. Moreover, the post 280 may be implemented as a push button comprising an internal spring (not shown) and one or more detents 282. The spring may bias the post 280 away from the top surface 262 and toward a locked position, in which the post 280 causes the one or more detents 282 to extend outwardly from a surface of the post 280. Such extended detents 282 may engage the recess 124 of port 122 or the recess 134 of port 132 when the post 280 is placed in the respective port 122, 132. Such engagement may prevent sliding the post 280 from the respective port 122, 132 and may prevent removal of the arm 250 from the rack 110. However, in various embodiments, a person may push the post 280 toward the top surface 262 to overcome the biasing force of the spring and place the post 280 into a released position. In the released position, the post 280 may permit inward deflection of the detents 282 by the wall of the ports 122, 132 and may permit sliding the arm 250 off the post 280. Thus, the post 280 permits easy attachment of the arm 250 to the rack 110 since a person needs to merely slide the port 122, 132 over the post 280 in order to snap the arm 250 to the rack 110. Similarly, the post 280 permits easy detachment of the arm 250 from the rack 110 since a person needs to merely press the post 280 in order to release the detents 282 and permit the arm 250 to be slid off the post 280.

As shown in the cross-section of FIG. 5, the distal portion 270 of the second arm 250 may further include a button 290, a pivot pin 292, retaining pin 294, and a spring 296. The pivot pin 292 may extend through lateral sides of the distal portion 270 and through a pivot hole 291 of the button 290. The pivot hole 291 may closely mate with a longitudinal surface of the pivot pin 292 in order to provide an axis about which the button 290 may pivot or rock. Similarly, the retaining pin 294 may extend through lateral sides 272 of the distal portion 270 and through a retaining hole 293 of the button 290. The retaining hole 293 may be larger than longitudinal surfaces of the retaining pin 294 in order to provide the button 290 with a range of movement about the axis of the pivot pin 292. In this manner, the button 290 may pivot about the pivot pin 292, but the retaining pin 294 may cooperate with the retaining hole 293 to limit movement of the button 290 between a fully engaged position and a fully disengaged position.

The spring 296 may be positioned between a proximal end 295 of the button 290 and a seat 273 of the distal portion 270. In various embodiments, the spring 296 comprises a compression spring that supplies a biasing force that biases the proximal end 295 upward and toward the fully engaged position. In the fully engaged position, a distal end 297 of the button 290 may extend into a channel 274 of the distal portion 270. In such an engaged position, the distal end 297 of the button 290 may engage teeth 310 of the tower 300 and retain the tower 300 at a specific position. A person, however, may press the proximal end 295 of the button 290 to move the button 290 toward the fully disengaged position. In the fully disengaged position, the distal end 297 of the button 290 may move away from the teeth 310 of the tower 300 so as to permit sliding the tower 300 along the channel 274.

As shown in FIG. 6, the tower 300 may be fully disengaged from the arm 250 by simply pressing the button 290 and sliding the tower 300 downward and/or the arm 250 upward. Conversely, a person may press the button 290 in order to slid the arms 200, 250 down respective towers 300 in order to place the arms 200, 250 closer to anatomical structures to which the arms 200, 250 are coupled via their respective towers 300 as shown in FIGS. 7 and 8. Such a lowered position may provide at least two advantages. One, the lowered position may position the arms 200, 250 out of surgeon's line of sight thus improving the surgeon's view of the operative site. Two, the lower position may improve the arms 200, 250 ability to impart compression forces and/or distraction forces upon the anatomical structures to which they are attached since the lower position effectively places the arms 200, 250 closer to the anatomical structures.

Referring back to FIGS. 5 and 6, the tower 300 may comprise a generally-cylindrical tube shape body 301 with a central longitudinal bore 302 between an upper end and a lower end of the body 301. Further, the tower 300 may comprise a track 305 that runs longitudinally down a proximal side of the body 301, a first vertical slit 331 runs longitudinally down a first lateral side of the body 301, and a second slit 331 runs longitudinally down a second lateral side of the body 301 and opposite the first slit 331.

The two vertical slits 331 may extend through the lower end of the body 301 and their respective lateral sides of the body 301. However, as shown, the two vertical slits 331 do not extend all of the way to the upper end of the body 301. As such, the vertical slits 331 effectively split the body 301 into two cantilevered fingers 333. As explained in greater detail below, the lower ends of the fingers 333 may be configured to grasp a pedicle screw 30 and lock the pedicle screw 30 to the tower 300.

A shown, the track 305 comprises teeth 310 that are flanked by rails 320. In various embodiments, the rails 320 are formed by longitudinal recesses 321 into the body 301. In particular, each recess 321 may extend into the outer surface of the body 301 at an angle such that a distance between the opposing recesses is greater at an outer surface of the body 301 than at their depths. Moreover, each recess 321 may comprise an upper end 322 and a lower end 324. The upper ends 322 may provide openings for the arms 200, 250 to enter and grasp the rails 320. In particular, such openings may be sized and spaced to receive respective flanges or fingers 276 of the channel 274 that runs through the distal portion 270 of the arm 250.

The fingers 276 of the distal portion 270 may be angled inward toward the channel 274 so as to closely mate with and engage the rails 320 via the recesses 321 when the channel 274 receives the track 305. In this manner, the fingers 276 may capture the rails 320 and position the track 305 in its channel 274. In various embodiments, the opening of the upper ends 322 may be tapered such that the opening provided at the upper end 322 is larger than the opening or groove provided by the recess 321. Such tapering may make it easier for a person to slide the fingers 276 into the recesses 321 and engage the rails 320 with the fingers 276 of the arm 250.

In various embodiments, the lower end 324 of each recess 321 is closed. Such closing of the lower end 324 effectively provides a lower stop that prevents sliding the fingers 276 off the lower end of the rails 320 and disengaging the fingers 276 from the rails 320 in the process. In this manner, a person does not need to be concerned about inadvertently disengaging the arms 200, 250 from the towers 300 when sliding the arms 200, 250 toward a lower position closer to the attached anatomical structures.

As described above, the arms 200, 250 may engage rails 320 of respective towers 300 in a manner that permits the arms 200, 250 to translate longitudinally along the respective tower 300 while firmly coupling the tower 300 to the rack 110. However, in other embodiments, the arms 200, 250 may be implemented to utilize different techniques and/or mechanisms to couple the tower 300 to rack 110.

For example, the arms 200, 250 may engage the towers 300 via a male/female T-slot connection in which the arms 200, 250 comprise a male T-shaped member that engages a female T-shaped slot of the tower 300. Conversely, the tower 300 may comprise a male T-shaped member that engages a female T-shape slot of the arms 200, 250.

Alternatively, the arms 200, 250 may engage the towers 300 via a cam lock mechanism that grips an outer diameter of the towers 300. Such a cam lock mechanism would not need to completely circumscribe the outer diameter. For example, the cam lock mechanism may comprise a cam that pulls fingers of the arms 200, 250 toward each other to grasp the tower or rails of the tower in a manner similar to the above described fingers.

In yet another embodiment, the tower 300 may include holes spaced along its longitudinal length. Actuation of a lever, button, or other mechanism of the arm 200, 250 may control extension/retraction of pin of the arm 200, 250. Extension of the pin into one of the holes of the tower 300 may restrict further translation of the arm 200, 250 along the tower 300 until the lever, button, other mechanism is actuated to retract the pin from the hole. In a further embodiment, the arms 200, 250 may operate as a crab clamp in which rotation of screw in a first direction may cause fingers or other members of the arms 200, 250 to grasp the tower 300 and rotation of the screw in a second direction may cause the fingers or other members of the arms 200, 250 to release the tower 300.

Figure 10:
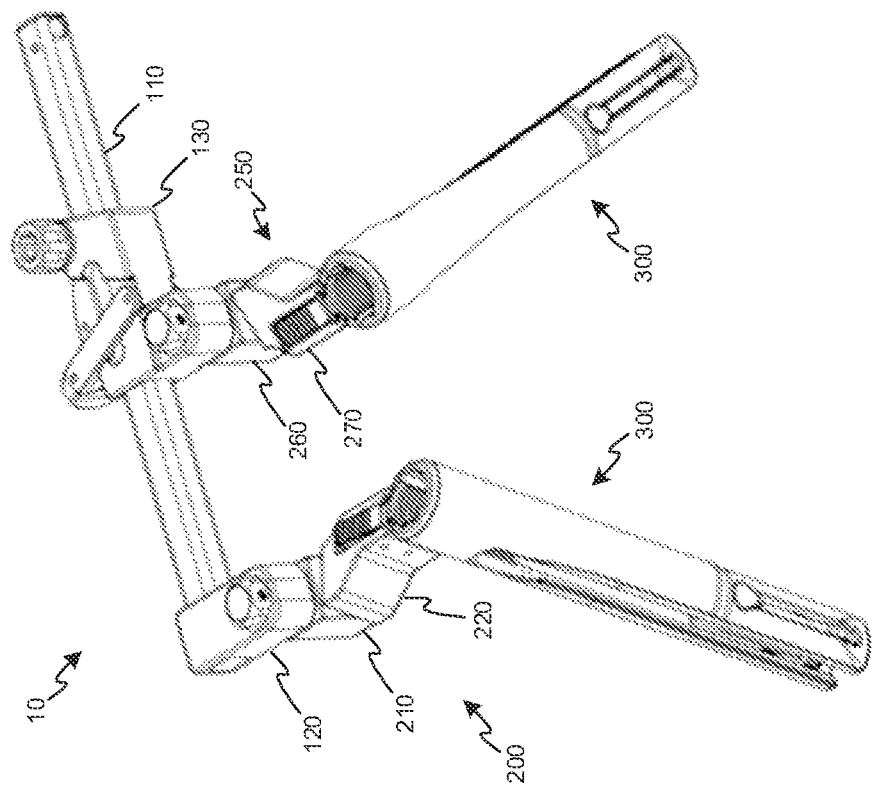
FIG. 10 provides a perspective view of the surgical instrument depicted in FIG. 1 with its arms angled outwards.
Figure 9:
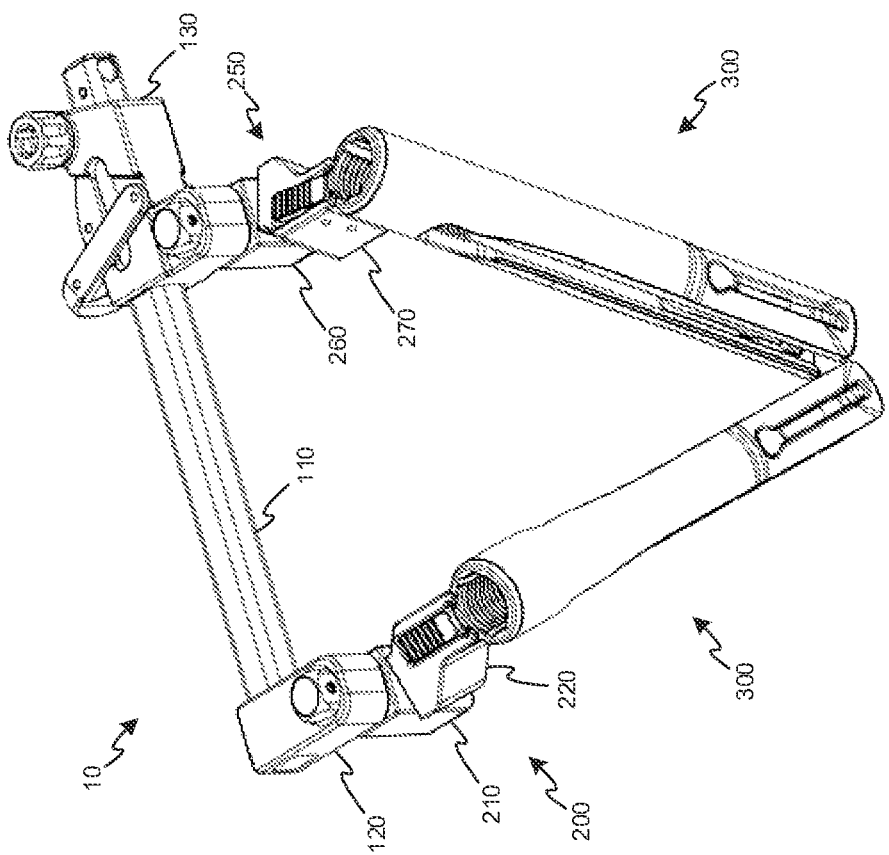
FIG. 9 provides a perspective view of the surgical instrument depicted in FIG. 1 with its arms angled inwards.
Figure 11C:
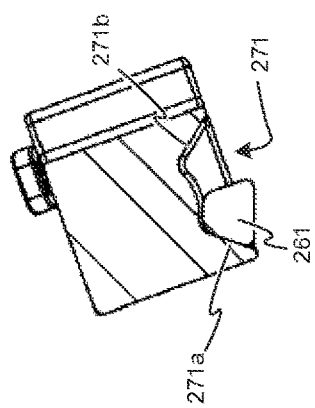
FIGS. 11A-11E provide various views of a pivot joint that permits angling of arms per FIGS. 9 and 10.
Figure 11B:
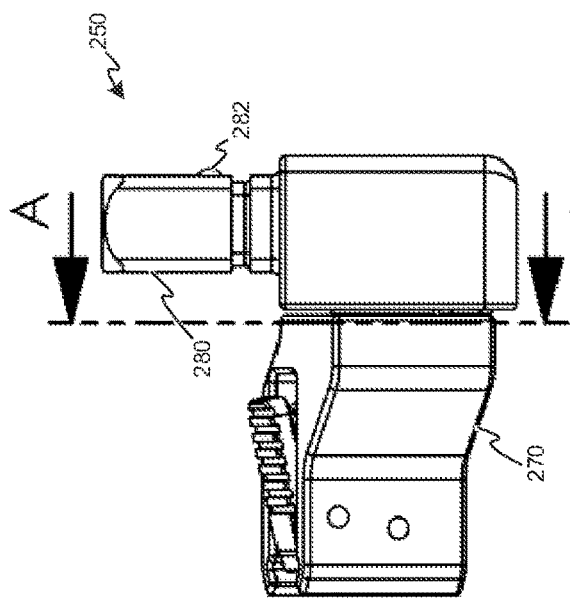
Figure 11E:
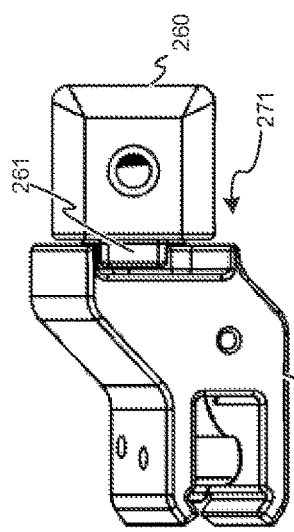
Figure 11A:
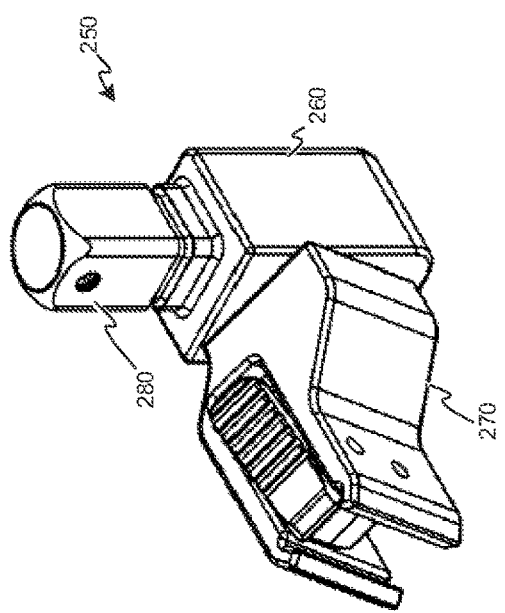
Figure 11D:
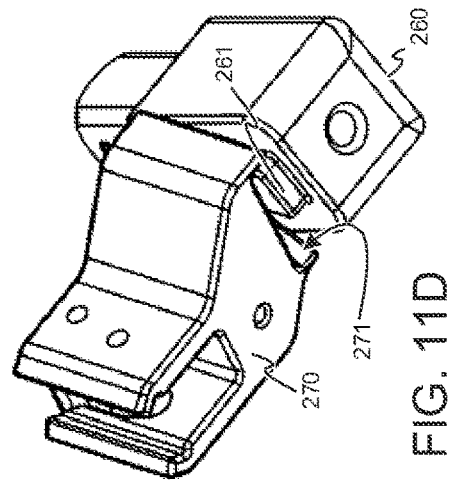

As shown in FIG. 6, the proximal portion 260 of the second arm 250 may be pivotally coupled to its distal portion 270 via a pin 264. In particular, the pin 264 may provide an axis of rotation that runs longitudinally through the second arm 250. Thus, the axis of rotation provided by the pin 264 may be perpendicular to, intersect, or otherwise cross a longitudinal axis of the rack 110 when attached to the rack 110. See, e.g., FIGS. 9 and 10. In particular, FIG. 9 depicts the distal portions 220, 270 of the arms 200, 250 angled such that lower ends of their respective towers 330 are angled toward each other. Conversely, FIG. 10 depicts the distal portions 220, 270 of the arms 200, 250 angled such that the lower ends of their respective towers 300 are angled away from each other.

Details of a pivot joint between the proximal portion 260 and distal portion 270 of the second arm 250 are shown in FIGS. 11A-11E. As shown, the distal portion 270 of the arm 250 may include a track or recess 271 in a proximal surface of the distal portion 270. The track 271 may laterally traverse the proximal surface between a first end or stop 271a and a second end or stop 271b of the track 271. Conversely, the proximal portion 260 of the arm 250 may include a projection, member, or tab 261 that extends or protrudes from a distal surface of the proximal portion 260. The tab 261 may engage the track 271. In one embodiment, the distal portion 270 may rotate with respect to the proximal portion 260 of the arm 250 about the pin 264. However, the ends 271a, 271b of the track 271 may engage the tab 261 and limit rotation to a predetermined range of rotation (e.g., ±20°, ±15°, etc.). FIGS. 11A-11E depict the track 271 in the distal portion 270 and the tab 261 in the proximal portion 260. However, in other embodiments, the distal portion 270 may have the tab and the proximal portion 260 may have the track.

The pivot join of FIGS. 11A-11E generally permits free rotation within the predetermined range. The pivot joint of FIGS. 12A-12F depicts an alternative in which the rotation between the distal portion 270 and the proximal portion 260 may be adjusted and locked to a desired angle. To this end, an angling mechanism 240 may adjust an angle of rotation between the distal portion 270 and the proximal portion 260. In particular, the angling mechanism 240 may include an adjustment screw 242 that passes vertically through the proximal portion 260 of the arm 250. In the depicted embodiment, the adjustment screw 242 comprises a shaft 243 having a threaded upper portion 244 and a lower portion 245. A bobbin 246 is coupled to the lower portion 245 of the shaft 243. A head 247 is coupled to an upper end of the shaft 243. Due to the threaded portion 244, rotation of the head 247 in a first direction extends the bobbin 246 in a downward direction and rotation of the head 247 in an opposite second direction retracts the bobbin 246 in upward direction.

The angling mechanism 240 further includes members or tines 248 that protrude from the distal portion 270 of the arm 250 and engage tapered surfaces 249 of the bobbin 246. Due to such engagement, as the the bobbin 246 is moved downward due to rotation of head 247, the distal portion 270 is rotated in a first direction with respect to the proximal portion 260 of the arm 250. Conversely, as the the bobbin 246 is moved upward due to rotation of head 247, the distal portion 270 is rotated in a second direction that is opposite to the first direction. Via rotation of the head 247, a person may adjust a rotation of the distal portion 270 with respect to the proximal portion 260.

Figure 14:
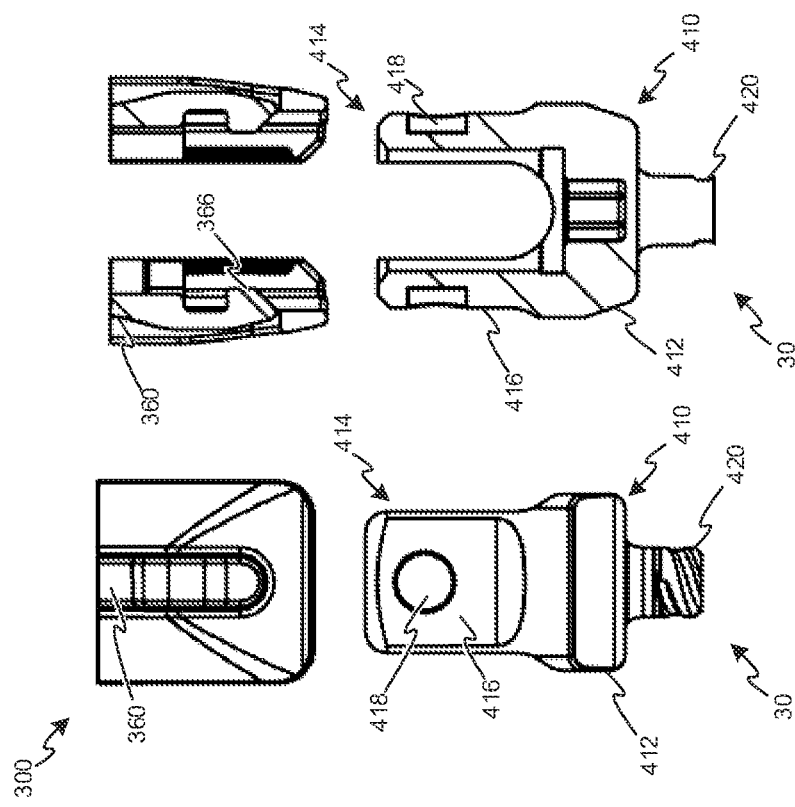
FIG. 14 provides a magnified view of the tower and pedicle screw of FIG. 11.
Figure 13:
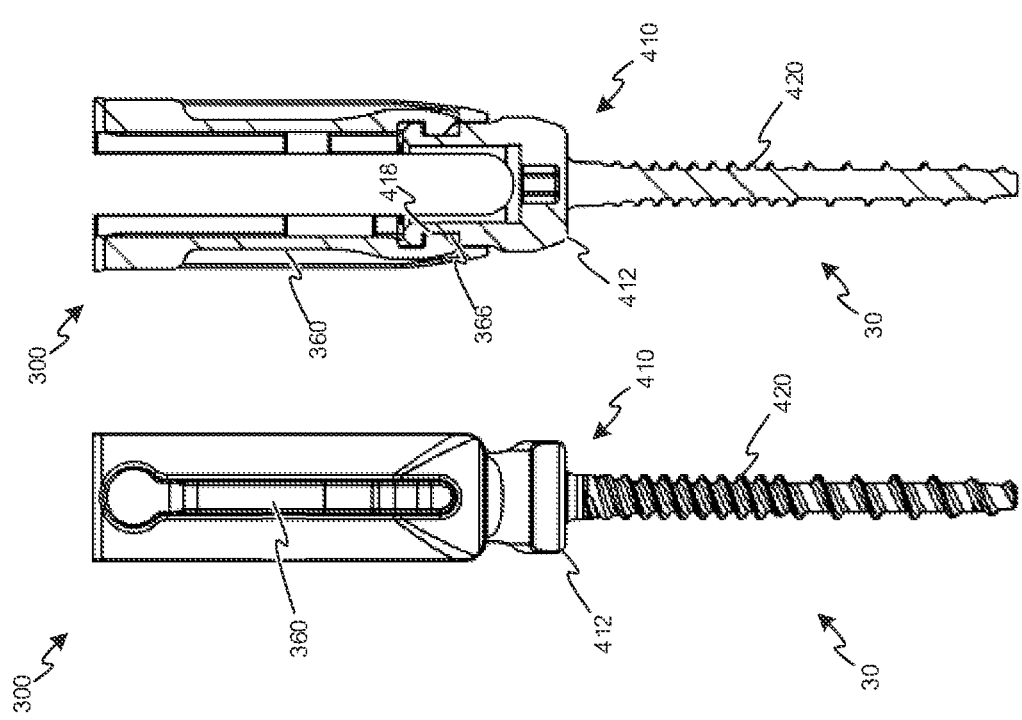
FIG. 13 provides a perspective view and corresponding cross-section of a tower of the surgical instrument depicted in FIG. 1 coupled to a pedicle screw.

Referring now to FIGS. 13 and 14, aspects of a pedicle screw 30 will be explained. As shown, the pedicle screw 30 may include a head 410 and a threaded shaft 420. The head 410 may comprise a generally cylindrical base 412 coupled to a proximal end of the threaded shaft 420. In various embodiments, the base 412 is coupled to the shaft 420 such that a longitudinal axis of the base 412 and a longitudinal axis of the shaft 420 are coaxially aligned. As such, rotation of the head 410 about the longitudinal axis of the base 412 imparts rotation of the threaded shaft 420 about its longitudinal axis. In this manner, a distal end of the threaded shaft 420 may be driven into an anatomical structure such as a vertebrae.

As further shown, the head 410 may comprise wings or tabs 414 that vertically extend above the base 412. As shown, a lower end of each tab 414 is coupled to the base 412. Moreover, each tab 414 includes an outer vertical surface 416 between the lower end and the upper end of the respective tab 414. As further shown, the outer vertical surface 416 includes a hole or recess 418 which is configured to receive a detent 366 of the tower 300.

As noted above, the cantilevered fingers 333 may lock the tower 300 to the pedicle screw 30. In general, each cantilevered finger 333 may include structures for grasping and locking to a pedicle screw 30. Moreover, each cantilevered finger 333 may include structures that release the pedicle screw 30 in response to interactions with the removal tool 20. In various embodiments, the fingers 333 may be implemented in a similar.

As shown, the finger 333 may include a leaf spring 360. In various embodiments, the leaf spring 360 may be integrally-formed from a side of the tower body 301. Regardless of whether integrally-formed, the leaf spring 360 may include an upper end 362 coupled to the tower body 301 and a lower end 364 radially biased toward the bore 302 of the tower body 301. Moreover, the lower end 364 of the leaf spring 360 comprises a detent 366 configured to engage the pedicle screw 30 and lock the tower 300 to the pedicle screw 30. In various embodiments, the detent 366 is tapered such that the detent 366 gradually slopes from its lower end to its upper end inward toward the bore 302. Such gradual slope may permit a pedicle screw 30 received via the lower end of the tower 300 to press against the sloped surface and overcome the biasing force of the leaf spring 360. Conversely, the detent 366 may provide an upper end with an abrupt transition between a base of the detent 366 and a distal end. Such abrupt surface may prevent a pedicle screw 30 from overcoming the bias force of the leaf spring 360 when pressed against the abrupt surface through an attempt to extract the pedicle screw 30 from the tower 300.

As noted above, the leaf spring 360 biases the lower end 364 and its detent 366 toward the bore 302. As such, when the lower end of the tower 300 is placed over the head 410 of the pedicle screw 30, the tabs 414 may overcome the bias of the leaf spring 360 and force the lower end 364 away from the bore 302. Once the recess 418 aligns with a detent 366, the leaf spring 360 may move or snap the detent 366 back toward the bore 302 and into the recess 418. Such snapping may be felt and heard by the person attaching the tower 300 to the pedicle screw 30. Thus, the leaf spring 360 and detent 366 may provide both audible and tactile feedback regarding a proper coupling of the tower 300 to the pedicle screw 30.

The pedicle screw 30 is depicted with two opposing tabs 414. However, various embodiments of the pedicle screw 30 may include a different number of tabs 414 and/or recesses 418. For example, the head 410 may include a single tab 414 that circumscribes or mostly circumscribes the head 410. Such a single tab 414 may include one or more recesses 418 to capture retaining detents 366 of the tower 300. Furthermore, while the head 410 is depicted with two recesses 418 positioned to receive corresponding detents 366 of the tower 300, some embodiments may not have a one-to-one correspondence between recesses 418 and detents 366. For example, the head 410 may include a greater number of recesses 418 so as to permit locking the tower 300 to the pedicle screw 30 via multiple orientations.

As explained above, a person may effectively snap the tower 300 onto the pedicle screw 30 without the aid of a tool. However, due to the abrupt upper surfaces of the detents 366, a person may not simply snap the tower 300 off the pedicle screw 30 once attached. Instead, in various embodiments, a person uses a removal tool 20 to disengage the detents 366 from the pedicle screw 30 in order to remove the tower 300 from the pedicle screw 30. As shown in FIGS. 15A-15E, the removal tool 20 may include a handle 500 and a shaft 510. The shaft 510 may include an upper end coupled to the handle 500. The shaft 510 may further include a keyed lower end 520. Furthermore, the removal tool 20 may include a shoulder 530 toward the upper end of the shaft 510.

During removal, the removal tool 20 may be positioned above the tower 300 as shown in FIG. 15A and inserted into the bore 302 of the tower 300 as shown in FIG. 15B. The removal tool 20 may be further inserted into the bore 302 until the shoulder 530 engages an upper surface of the tower 300 as shown in FIG. 15C. In various embodiments, the shoulder 530 is positioned along the shaft 510 such that the keyed lower end 520 is properly positioned within the bore 302 when the shoulder 530 engages the upper surface of the tower 300.

Figure 16C:
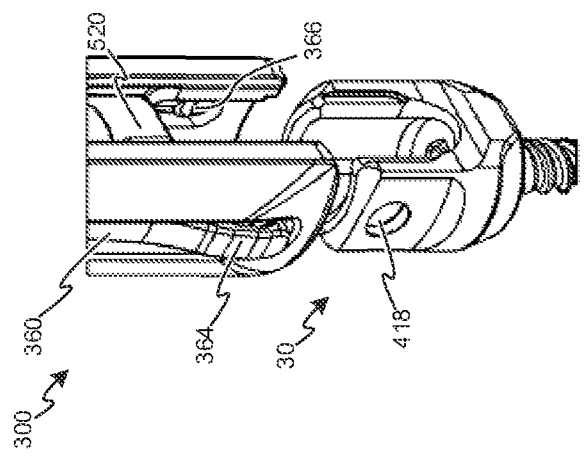
FIGS. 16A-16C depict the removal tool disengaging a tower of the surgical instrument of FIG. 1 from a pedicle screw.
Figure 16B:
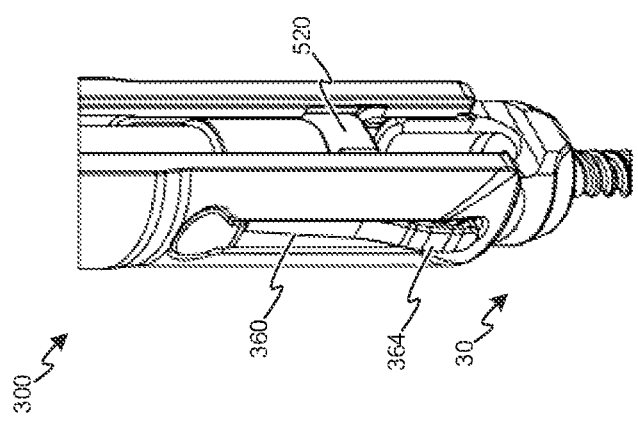
Figure 16A:
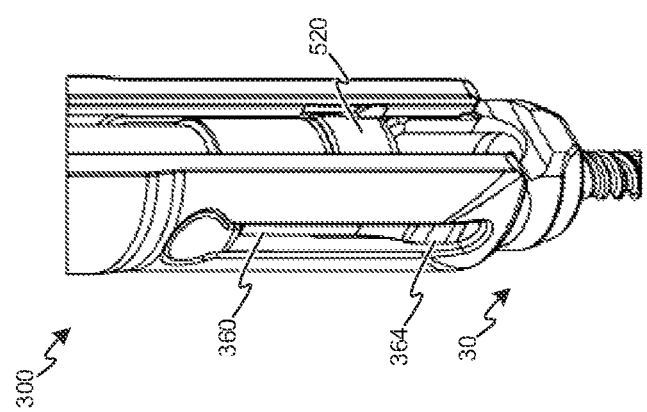

Once properly seated, the handle 500 may be rotated in order to rotate the keyed lower end 520 as shown in FIGS. 15D, 16B, 18. As shown in FIGS. 16B and 18, the keyed lower end 520 may engage the leaf springs 360 and force them radially outward from the bore 302 of the tower 300. Such outward movement of the leaf springs 360 may disengage the detents 366 from the recesses 418 of the pedicle screw 30. With the recesses 418 disengaged, the tower 300 along with the removal tool 20 may be removed from the pedicle screw 30 as shown in FIGS. 15E and 16C.

In various embodiments, the tower 300 may include stops 370 that prevent rotation of the keyed lower end 520 in a clockwise direction and grooves 372 that permit rotation of the keyed lower end 520 in counterclockwise direction. See, e.g., FIGS. 17 and 18. Moreover, the tower 300 may include stops 374 that prevent over rotation of the removal tool 20 passed the desired 90° rotation.

Figure 19:
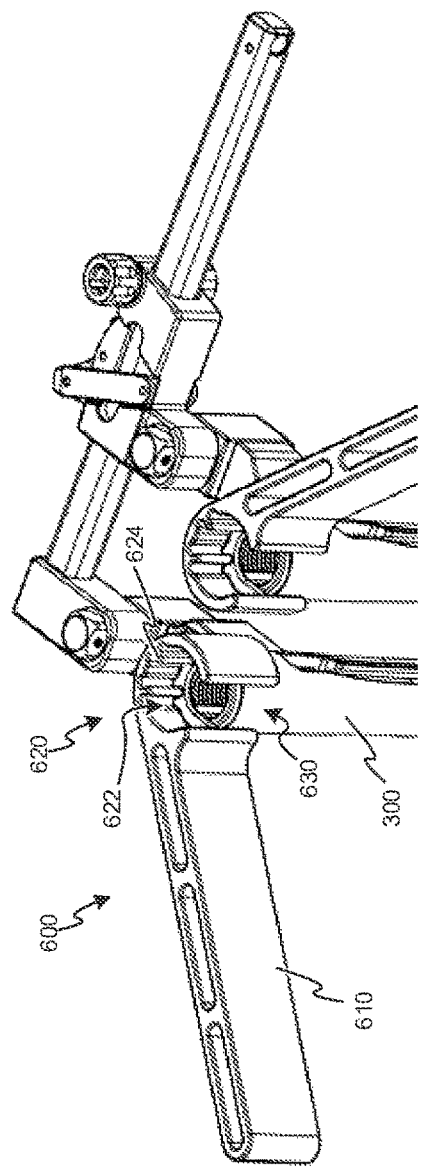
FIG. 19 provides a perspective view of counter torque tools engaged with upper ends of towers of the surgical instrument of FIG. 1.
Figure 20:
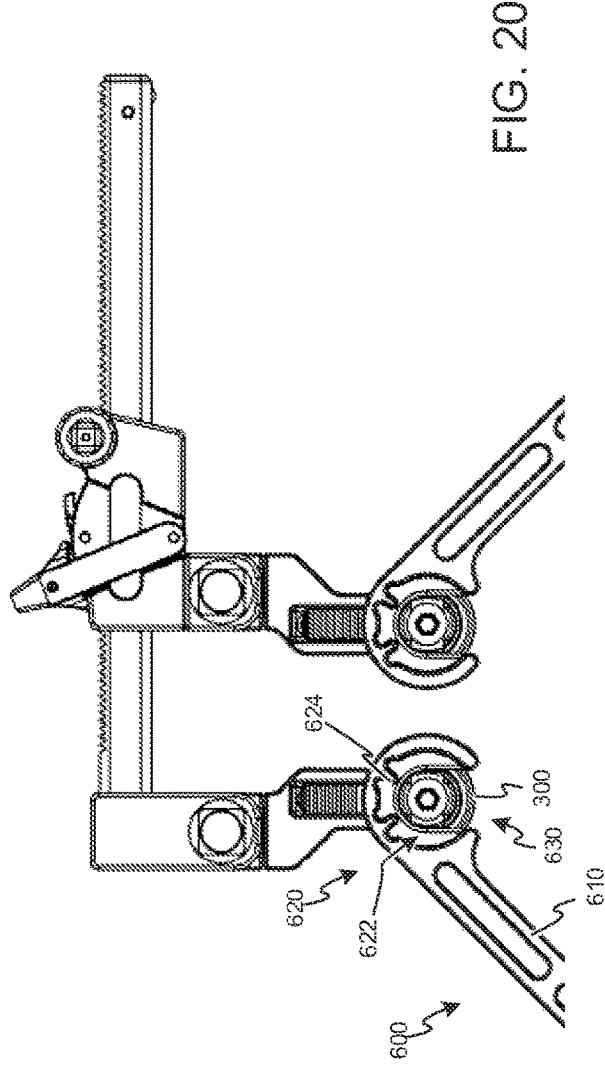
FIG. 20 provides a top view of counter torque tools engaged with upper ends of towers of the surgical instrument of FIG. 1.

Referring now to FIGS. 19 and 20, counter torque tools 600 coupled to towers 300 are shown. As shown, each counter torque tool 600 may include a handle 610 that extends from a connector 620. The connector 620 may include a recess 622 shaped to mate with an upper end of the tower 300. In particular, the recess 622 may have fingers 624 that engage rails 320 of the tower 300. Due to such engagement of rails 320, rotation of the tower 300 about its longitudinal axis translates into rotation of the handle 610 via its connector 620. Thus, a person may prevent rotation of the tower 300 by holding the handle 610 in a stationary position and/or applying a proper counter torque to the handle 610 of the counter torque tool 600. For example, a person may provide a proper counter torque to the tower 300 via tool 600 to prevent rotation of the tower 300 about its longitudinal axis when tightening a pedicle screw 30 to which the tower 300 is attached.

As further shown, a sidewall of the connector 620 may not completely circumscribe the tower 300. The opening 630 in the sidewall may permit viewing the upper end of the tower 300 while coupling the counter torque tool 600 to the tower 300. Such viewing may aid when trying to properly aligning the connector 620 with the upper end of the tower 300. However, in some embodiments, the connector 620 may be implemented without opening 630.

Moreover, FIGS. 19-20 depicted two counter torque tools 600 which appear to have different offsets of the handle 610 with respect to the connector 620. However, per an embodiment, the two counter torque tools 600 are implemented in the same manner. The depicted difference between the two counter torque tools 600 is due to one being vertically flipped with respect to the other. In other words, the counter torque tool 600 coupled to the left-side tower 300 may be coupled to the right-side tower 300 in the same depicted configuration by merely flipping the tool 600 over. Thus, in one embodiment, there is not a right side tool and a left side tool, but a single tool that is suitable for engaging either tower 300.

Figure 22:
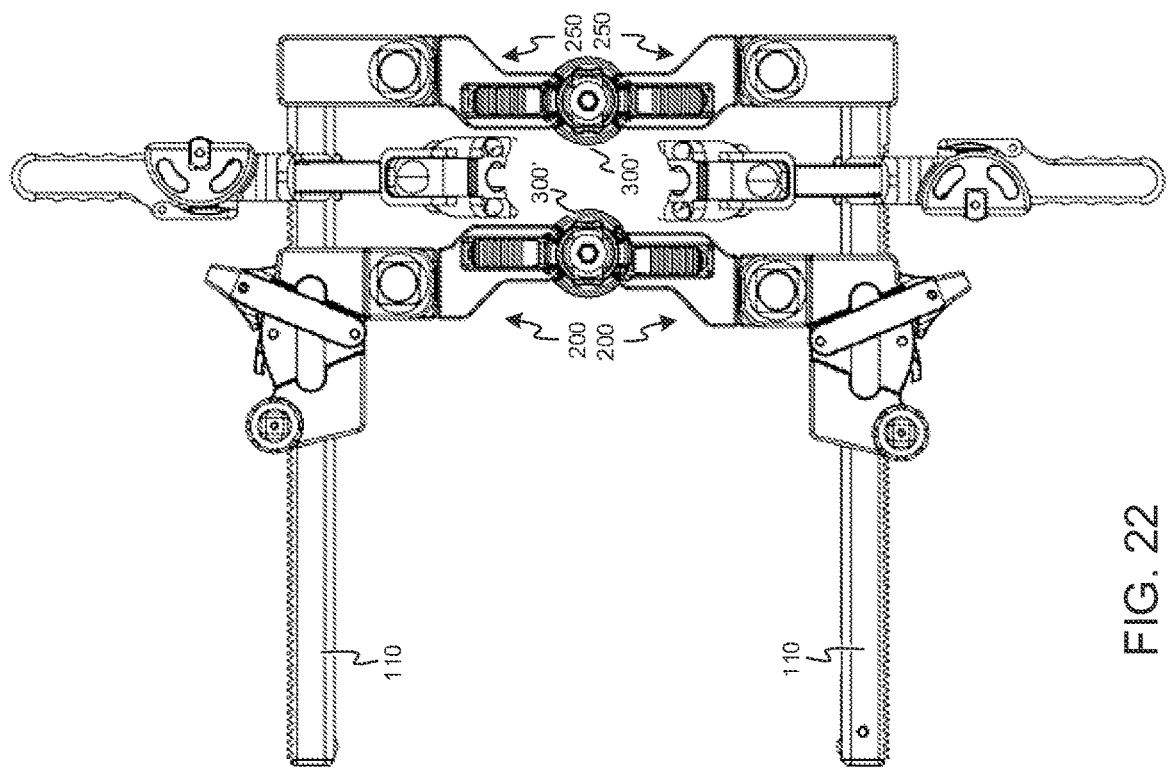
FIG. 22 provides a top of the surgical instrument of FIG. 21 in which towers have a second track to which accessories may be attached.
Figure 21:
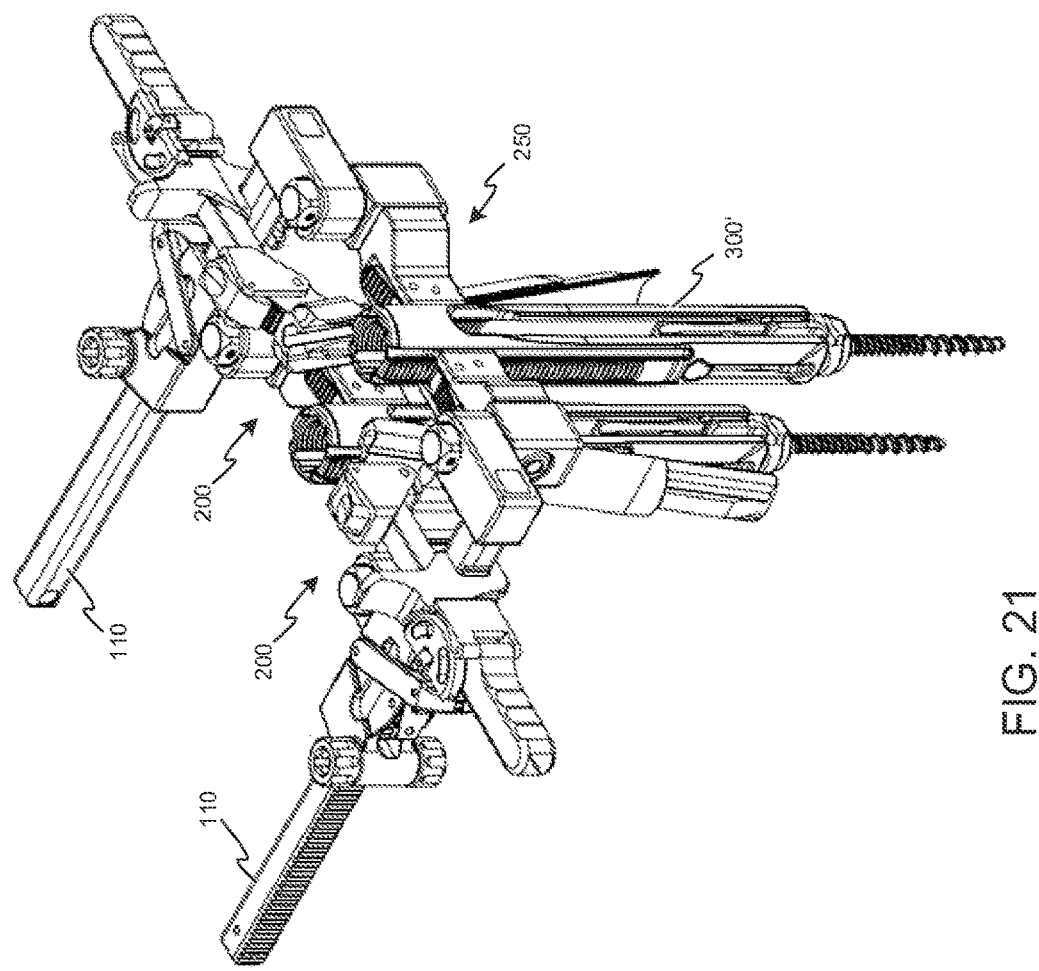
FIG. 21 provides a perspective view of a surgical instrument similar to the surgical instrument of FIG. 1 in which each tower has a second track to which an accessory is attached.

Finally, as shown in FIGS. 21-23, towers may include a plurality of tracks 305. As shown, towers 300' of FIGS. 21-23 may be implemented in the same manner as the towers 300 of FIG. 1, but may include a second track 305 opposite the track 305. The second track 305 may permit attaching various accessories to the towers 300'. In FIGS. 21 and 22, an additional rack 110 and arms 200, 250 are attached to the towers 300' via the second tracks 305. Moreover, as shown, retractor blades may be attached to the racks 110 at locations that are laterally between attachment points of the arms 200, 250. However, tracks 305 are not limited to merely the attachment of additional racks 110. Other accessories such as lights, smoke evacuation, retractor blades, etc. may be attached to towers 300' via their respective second tracks 305.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment or embodiments disclosed, but that the present invention encompasses all embodiments falling within the scope of the appended claims.

What is claimed is:

1. A surgical instrument, comprising:
   a rack comprising a rail having a rail first end and a rail second end;
   a first arm comprising a first arm proximal end, a first arm distal end, a first arm top side that extends from the first arm proximal end to the first arm distal end, a first arm bottom side that extends from the first arm proximal end to the first arm distal end, and a first arm channel in the first arm distal end, wherein the first arm proximal end is coupled to the rail toward the rail first end, and wherein the first arm channel passes through the first arm top side and the first arm bottom side;
   a second arm coupled to the rack via a second arm carriage, wherein the second arm carriage is configured to move the second arm along the rack;
   a spring-biased stop toward the rail second end, wherein a biasing force of the spring-biased stop is sufficient to prevent the second arm carriage from moving past the spring-biased stop based on a first force applied by weight of the second arm carriage but permits the second arm carriage to move past the spring-biased stop based on a second force that is greater than the first force; and
   a first tower comprising a first tower upper end, a first tower lower end, and a first tower track between the first tower upper end and the first tower lower end;
   wherein the first arm channel is configured to receive the first tower track and selectively position the first arm distal end along the first tower track; and
   wherein the first arm channel permits passage of the first tower into an upper end of the first arm channel, along the first arm channel, and out a lower end of the first arm channel such that the first tower track extends below the first arm bottom side.

2. The surgical instrument of claim 1, wherein the first tower lower end is configured to engage and snap onto a pedicle screw.

3. The surgical instrument of claim 2, wherein:
   the first tower comprises a bore that runs longitudinally between the first tower upper end and the first tower lower end; and
   the first tower is configured to disengage from the pedicle screw in response to a tool inserted into the bore of the first tower.

4. The surgical instrument of claim 2, wherein:
the first tower comprises a bore that runs longitudinally between the first tower upper end and the first tower lower end; and
the first tower is configured to disengage from the pedicle screw in response to rotation of a tool inserted into the bore of the first tower.

5. The surgical instrument of claim 1, wherein the first tower comprises a detent configured to secure a pedicle screw to the first tower when the pedicle screw is inserted into the first tower lower end.

6. The surgical instrument of claim 1, wherein:
the first tower includes a detent and a spring, wherein the spring applies a biasing force that biases the detent radially inward; and
the detent and the spring are configured to permit a pedicle screw to overcome the biasing force and move the detent radially outward as the pedicle screw is inserted into the first tower lower end.

7. The surgical instrument of claim 6, wherein the detent and the spring are configured to prevent the pedicle screw from overcoming the biasing force and moving the detent radially outward and out of a recess in the pedicle screw.

8. The surgical instrument of claim 1, wherein the second arm carriage comprises a pinion having teeth that engage teeth of the rack and move the second arm carriage along the rack based on rotation of the pinion.

9. The surgical instrument of claim 8, wherein:
the second arm carriage comprises a lever and a pawl;
the lever selectively engages the pawl with the teeth of the rack; and
the pawl, when engaged with the teeth of the rack, permits movement of the second arm carriage along the rack in a first direction but prevents movement of the second arm carriage along the rack in a second direction.

10. The surgical instrument of claim 1, wherein:
the first arm comprises a first arm proximal portion, a first arm distal portion, a first arm pivot joint that couples a proximal end of the first arm distal portion to a distal end of the first arm proximal portion; and
the first arm pivot joint permits rotation of the first arm distal portion about a first arm pivot axis that extends through the proximal end of the first arm distal portion and the distal end of the first arm proximal portion.

11. The surgical instrument of claim 10, wherein the first arm comprises one or more stops that limit rotation of the first arm distal portion about the first arm pivot axis.

12. The surgical instrument of claim 1, wherein the first tower comprises a first tower second track between the first tower upper end and the first tower lower end.

13. The surgical instrument of claim 12, comprising:
a third arm comprising a third arm proximal end and a third arm distal end;
wherein the third arm distal end comprises a third arm channel; and
wherein the third arm channel is configured to receive the first tower second track and selectively position the third arm distal end along the first tower second track.

14. The surgical instrument of claim 12, comprising an accessory coupled to the first tower second track and configured to selectively position the accessory along the first tower second track.

15. A system, comprising:
a removal tool comprising a handle and a shaft, wherein the shaft comprises an upper end coupled to the handle and a keyed lower end; and
a surgical instrument comprising a rack comprising a rail having a rail first end and a rail second end, a first arm coupled to the rack, a second arm coupled to the rack via a second arm carriage, a spring-biased stop toward the rail second end, a first tower coupled to the first arm, and a second tower coupled to the second arm;
wherein the first arm comprises a first arm proximal end, a first arm distal end, a first arm top side that extends from the first arm proximal end to the first arm distal end, a first arm bottom side that extends from the first arm proximal end to the first arm distal end, and a first arm channel in the first arm distal end, wherein the first arm channel passes through the first arm top side and the first arm bottom side;
wherein the first tower comprises a first tower upper end, a first tower lower end, and a first tower track comprising a first tower track upper end and a first tower track lower end between the first tower upper end and the first tower lower end;
wherein the first arm channel is configured to receive the first tower track and selectively position the first arm distal end along the first tower track;
wherein the first arm channel permits passage of the first tower track lower end into an upper end of the first arm channel, along the first arm channel, and out a lower end of the first arm channel such that the first tower track lower end extends below the first arm bottom side; and
wherein the first tower lower end is configured to directly engage a pedicle screw and is configured to disengage from the pedicle screw in response to the removal tool being inserted into the first tower;
wherein the second arm carriage is configured to move the second arm along the rack; and
wherein a biasing force of the spring-biased stop is sufficient to prevent the second arm carriage from moving past the spring-biased stop based on a first force applied by weight of the second arm carriage but permits the second arm carriage to move past the spring-biased stop based on a second force that is greater than the first force.

16. The system of claim 15, wherein:
the first tower comprises a bore that runs longitudinally between the first tower upper end and the first tower lower end; and
the first tower is configured to disengage from the pedicle screw in response to the removal tool being inserted into the bore of the first tower.

17. The system of claim 15, wherein:
the first tower comprises a bore that runs longitudinally between the first tower upper end and the first tower lower end; and
the first tower is configured to disengage from the pedicle screw in response to rotation of the removal tool in the bore of the first tower.

18. The system of claim 17, wherein the removal tool comprises a shoulder positioned between the handle and the keyed lower end such that the keyed lower end of the removal tool is aligned with a keyed surface of the first tower when the shoulder engages an upper surface of the first tower and prevents further insertion of the removal tool into the bore.

19. The system of claim 18, wherein the keyed surface of the first tower and the keyed lower end cooperate to permit rotation of the removal tool in a first direction and prevent rotation of the removal tool in a second direction.

20. The system of claim 19, wherein the keyed surface comprises a stop that prevents rotation of the removal tool in the first direction beyond a screw removal position.

21. The system of claim 15, wherein the first tower comprises a detent configured to secure the pedicle screw to the first tower when the pedicle screw is inserted into the first tower lower end.

22. The system of claim 15, wherein:
the first tower includes a detent and spring that applies a biasing force that biases the detent radially inward; and
the detent is configured to permit the pedicle screw to overcome the biasing force and move the detent radially outward as the pedicle screw is inserted into the first tower lower end.

23. The system of claim 22, wherein the detent is configured to prevent the pedicle screw from overcoming the biasing force and moving the detent radially outward and out of a recess in the pedicle screw.

24. The system of claim 15, wherein the second arm carriage comprises a pinion having teeth that engage teeth of the rack and move the second arm carriage along the rack based on rotation of the pinion.

25. The system of claim 24, wherein:
the second arm carriage comprises a lever and a pawl;
the lever selectively engages the pawl with the teeth of the rack; and
the pawl, when engaged with the teeth of the rack, permits movement of the second arm carriage along the rack in a first direction but prevents movement of the second arm carriage along the rack in a second direction.

26. The system of claim 15, comprising:
a counter torque tool comprising a handle that extends from a connector;
wherein the connector is configured to detachably couple the handle to the first tower and translate rotation of the first tower about a longitudinal axis of the first tower to the handle; and
wherein the handle of the counter torque tool, when held in a stationary position while coupled to the first tower, prevents rotation of the first tower about the longitudinal axis.

27. A surgical instrument, comprising:
a rack comprising a rail having a rail first end and a rail second end;
a first tower comprising a first tower upper end, a first tower lower end, and a first tower track between the first tower upper end and the first tower lower end, wherein the first tower lower end is configured to engage and secure a pedicle screw to the first tower; and
a first arm comprising a first arm proximal end, a first arm distal end, a first arm top side that extends from the first arm proximal end to the first arm distal end, and a first arm bottom side that extends from the first arm proximal end to the first arm distal end;
a second arm coupled to the rack via a second arm carriage, wherein the second arm carriage is configured to move the second arm along the rack; and
a spring-biased stop toward the rail second end;
wherein a biasing force of the spring-biased stop is sufficient to prevent the second arm carriage from moving past the spring-biased stop based on a first force applied by weight of the second arm carriage but permits the second arm carriage to move past the spring-biased stop based on a second force that is greater than the first force;
wherein a length of the first tower track between the first tower upper end and the first tower lower end is greater than a distance between the first arm top side and the first arm bottom side at the first arm distal end; and
wherein the first arm distal end is configured to engage the first tower track and selectively position the first tower along the first arm distal end between the first tower upper end and the first tower lower end such that the first tower lower end protrudes beyond the first arm bottom side.

28. The surgical instrument of claim 27, wherein:
the first tower comprises a bore that runs longitudinally between the first tower upper end and the first tower lower end; and
the first tower is configured to disengage from the pedicle screw in response to a tool inserted into the bore of the first tower.

29. The surgical instrument of claim 27, wherein:
the first tower includes a detent and a spring, wherein the spring applies a biasing force that biases the detent radially inward; and
the detent and the spring are configured to permit a pedicle screw to overcome the biasing force and move the detent radially outward as the pedicle screw is inserted into the first tower lower end.

30. The surgical instrument of claim 29, wherein the detent and the spring are configured to prevent the pedicle screw from overcoming the biasing force and moving the detent radially outward and out of a recess in the pedicle screw.

* * * * *